(12) United States Patent
Lambeau et al.

(10) Patent No.: US 9,637,553 B2
(45) Date of Patent: May 2, 2017

(54) ANTI-SPLA2-IIA ANTIBODIES AND USES THEREOF

(71) Applicants: CENTRE NATIONAL DE LA RECHERCHE SCIENTIFIQUE (CNRS), Paris (FR); UNIVERSITE NICE SOHIA ANTIPOLIS, Nice (FR)

(72) Inventors: Gerard Lambeau, Grasse (FR); Emmanuel Valentin, Cachan (FR); Melanie Rennou, Orsay (FR)

(73) Assignees: CENTRE NATIONAL DE LA RECHERCHE SCIENTIFIQUE (CNRS), Paris (FR); UNIVERSITE NICE SOPHIA ANTIPOLIS, Nice (FR)

( * ) Notice: Subject to any disclaimer, the term of this patent is extended or adjusted under 35 U.S.C. 154(b) by 0 days.

(21) Appl. No.: 14/387,430

(22) PCT Filed: Mar. 22, 2013

(86) PCT No.: PCT/EP2013/056085
§ 371 (c)(1),
(2) Date: Sep. 23, 2014

(87) PCT Pub. No.: WO2013/139968
PCT Pub. Date: Sep. 26, 2013

(65) Prior Publication Data
US 2015/0086564 A1  Mar. 26, 2015

(30) Foreign Application Priority Data
Mar. 23, 2012  (EP) .................................. 12161036

(51) Int. Cl.
| | | |
|---|---|---|
| *C07K 16/40* | (2006.01) | |
| *G01N 33/53* | (2006.01) | |
| *C12N 5/16* | (2006.01) | |
| *C12N 15/63* | (2006.01) | |
| *G01N 33/573* | (2006.01) | |
| *C07K 14/47* | (2006.01) | |

(52) U.S. Cl.
CPC .............. *C07K 16/40* (2013.01); *C12N 5/163* (2013.01); *C12N 15/63* (2013.01); *G01N 33/53* (2013.01); *G01N 33/573* (2013.01); *C07K 14/47* (2013.01); *C07K 2317/92* (2013.01); *G01N 2333/918* (2013.01)

(58) Field of Classification Search
None
See application file for complete search history.

(56) References Cited

U.S. PATENT DOCUMENTS

| 5,229,275 | A | 7/1993 | Goroff ............................. 435/70 |
| 5,567,610 | A | 10/1996 | Borrebaeck ................... 435/240 |
| 5,641,870 | A | 6/1997 | Rinderknecht ............... 530/417 |
| 5,795,961 | A | 8/1998 | Wallace ........................ 530/350 |
| 6,162,963 | A | 12/2000 | Kucherlapati ................. 800/18 |
| 7,473,423 | B2 | 1/2009 | Rodriguez ..................... 424/142 |
| 7,858,752 | B2 | 12/2010 | Tu ................................. 530/387 |
| 8,372,640 | B2 | 2/2013 | Zanetti .......................... 435/328 |
| 2003/0185827 | A1 | 10/2003 | Rodriguez .................... 424/142 |
| 2007/0117774 | A1 | 5/2007 | Zanetti ............................ 514/44 |
| 2008/0131912 | A1* | 6/2008 | Tu ....................... C07K 16/109 435/7.2 |

FOREIGN PATENT DOCUMENTS

| EP | 0404097 | 12/1990 | |
| EP | 1798243 | 6/2007 | |
| WO | 93/11161 | 6/1993 | |
| WO | 2008/076994 | 6/2008 | |
| WO | WO 2010009403 A2 * | 1/2010 | ............ A61K 45/06 |
| WO | 2011/085002 | 7/2011 | |

OTHER PUBLICATIONS

Boder et al (2000. PNAS. 97(20): 10701-10705).*
Tickle et al, 2009. JALA. 14:303-307.*
Rudikoff et al (Proc Natl Acad Sci USA 1982 vol. 79 pp. 1979-1983).*
Pascalis et al (Journal of Immunology, 2002, vol. 169, pp. 3076-3084).*
Casset et al (Biochemical and Biophysical Research Communications, 2003, vol. 307, pp. 198-205).*
Vajdos et al (Journal of Molecular biology, 2002, vol. 320, pp. 415-428).*
Holm et al (Molecular Immunology, 2007, vol. 44, pp. 1075-1084).*
Chen et al. (Journal of Molecular Biology, 1999, vol. 293, pp. 865-881).*
Wu et al. (Journal of Molecular Biology, 1999, vol. 294, pp. 151-162).*
MacCallum et al. (Journal of Molecular. Biology, 1996, vol. 262, pp. 732-745).*
Roshwalb et al, 2014. Genetic Engineering & Biotechnology News, 3 pages as printed.*
Chen, et al., "Selection and Analysis of an Optimized Anti-VEGF Antibody: Crystal Structure of an Affinity-matured Fab in Complex with Antigen," J. Mol. Biol. (1999) 293, pp. 865-881.
Schier, et al., "Isolation of High-affinity Monomeric Human Anti-c-erbB-2 Single chain Fv Using Affinity-driven Selection," J. Mol. Biol. (1996) 255, pp. 28-43.
Yang, et al., "CDR Walking Mutagenesis for the Affinity Maturation of a Potent Human Anti-HIV-1 Antibody into the Picomolar Range," J. Mol. Biol. (1995) 254, pp. 392-403.
Valentin et al. Increasing molecular diversity of secreted phospholipases A(2) and their receptors and binding proteins. 2000, Bioch. Biophys. Act. 59-70.
Lambeau, G., and Gelb, M. H. Biochemistry and physiology of mammalian secreted phospholipases A2. 2008, Annu. Rev. Biochem. 77, 495-520.

(Continued)

*Primary Examiner* — Zachary Howard
(74) *Attorney, Agent, or Firm* — Norton Rose Fulbright US LLP

(57) ABSTRACT

The present invention relates to antibodies anti-sPLA2-IIA and uses thereof.

15 Claims, 5 Drawing Sheets

(56) References Cited

OTHER PUBLICATIONS

Nevalainen et al. Time-resolved fluoroimmunoassays of the complete set of secreted phospholipases A2 in human serum. (2005) Biochimica et Biophysica Acta 1733 (2-3): 210-223.
Marks et al. By-passing immunization. Human antibodies from V-gene libraries displayed on phage. J. Mol. Biol., 1991, 222(3):581-597.
Morrison et al. "Chimeric human antibody molecules: mouse antigen-binding domains with human constant region domains" Proc. Natl. Acad. Sci. USA, 1984, 81(21):6851-6855.
Jones et al. Replacing the complementarity-determining regions in a human antibody with those from a mouse Nature, 1986, 321(6069):522-525.
Riechmann et al. Reshaping human antibodies for therapy. Nature, 1988, 332(6162):323-329.
Zapata et al. Engineering linear F(ab')2 fragments for efficient production in *Escherichia coli* and enhanced antiproliferative activity. Protein Eng. 1995, 8(10): 1057-1062.
Green et al. Antigen-specific human monoclonal antibodies from mice engineered with human Ig heavy and light chain YACs Nature Genet., 1994, 7(1):13-21.
Lonberg et al. Antigen-specific human antibodies from mice comprising four distinct genetic modifications. Nature, 1994, 368(6474):856-9.
McCafferty et al. Phage antibodies: filamentous phage displaying antibody variable domains. Nature, 1990, 348(6301):552-554.
Holliger et al. Diabodies: small bivalent and bispecific antibody fragments Proc. Natl. Acad. Sci. USA, 1993, 90(14):6444-6448.
Leong et al. Adapting pharmacokinetic properties of a humanized anti-interleukin-8 antibody for therapeutic applications using site-specific pegylation. Cytokine, 2001, 16(3):106-119.
Delgado et al Enhanced tumour specificity of an anti-carcinoembrionic antigen Fab' fragment by poly(ethylene glycol) (PEG) modification. Br. J. Cancer, 1996, 73(2):175-182.
Verhoeyen et al Reshaping human antibodies: grafting an antilysozyme activity. Science, 1988, 239(4847):1534-6.
Sims et al. A humanized CD18 antibody can block function without cell destruction. J. Immunol., 1993, 151(4):2296-308.
Carter et al. Humanization of an anti-p185HER2 antibody for human cancer therapy. PNAS, 1992, 89(10):4285-9.
Presta et al. Humanization of an antibody directed against IgE. J Immunol., 1993, 151(5):2623-32.
Jakobovits et al. Germ-line transmission and expression of a human-derived yeast artificial chromosome. Nature, 1993, 362(6417):255-8.
Othman et al. Human non-pancreatic (group II) secreted phospholipase A2 expressed from a synthetic gene in *Escherichia coli*: characterisation of N-terminal mutants. Biochim Biophys Acta Sep. 27, 1996;1303(2):92-102.
Bezzine et al. Exogenously added human group X secreted phospholipase A(2) but not the group IB, IIA, and V enzymes efficiently release arachidonic acid from adherent mammalian cells. J. Biol. Chem. Feb. 4, 2000;275(5):3179-91.
Singer et al Interfacial kinetic and binding properties of the complete set of human and mouse groups I, II, V, X, and XII secreted phospholipases A2. J Biol Chem. Dec. 13, 2002;277(50):48535-49.
Koduri et al, Bactericidal properties of human and murine groups I, II, V, X, and XII secreted phospholipases A(2). J Biol Chem Feb. 22, 2002;277(8):5849-57.
Rouault et al Recombinant production and properties of binding of the full set of mouse secreted phospholipases A2 to the mouse M-type receptor. Biochemistry Feb. 13, 2007;46(6):1647-62.
Lousse JC et al Expression of eicosanoid biosynthetic and catabolic enzymes in peritoneal endometriosis. Hum Reprod. Mar. 2010;25(3):734-41.
Yoshikawa T et al Cellular localization of group IIA phospholipase A2 in rats. J Histochem Cytochem. Jun. 2001;49(6):777-82.
Murakami M et al Functional association of type IIA secretory phospholipase A(2) with the glycosylphosphatidylinositol-anchored heparan sulfate proteoglycan in the cyclooxygenase-2-mediated delayed prostanoid-biosynthetic pathway. J Biol Chem, Oct. 15, 1999;274(42):29927-36.
Munoz MN et al Characterization of monoclonal antibodies specific for 14-kDa human group V secretory phospholipase A2 (hVPLA2). Hybridoma. Apr. 2000;19(2):171-6.
Munoz MN Quantitation of secretory group V phospholipase A(2) in human tissues by sandwich enzyme-linked immunosorbent assay. J Immunol Methods. Apr. 1, 2002;262(1-2):41-51.
Munoz MN Secretory group V phospholipase A2 regulates acute lung injury and neutrophilic inflammation caused by LPS in mice Am J Physiol Lung Cell Mol Physiol. Jun. 2009; 296(6):L879-87.
Cayman chemicals sPLA2 (human Type IIA) Monoclonal Antibody (Clone SCACC353) 2012.
Rodriguez et al. Database Geneseq "Mouse anti IGM antibody A2B5 kappa light chain cDNA".
Degiysee et al, "Groups IV, V, and X phospholipases A2s in human neutrophils: role in eicosanoid production and gram-negative bacterial phospholipid hydrolysis", Journal of biological chemistry, 2002, 277(7):5061-73.
Haas et al, "Characterization and differentiation-dependent regulation of secreted phospholipases A in human keratinocytes and in healthy and psoriatic human skin". Journal of investigative dermatology 2005, 124(1):204-11.
Henderson et al, "Blockade of human group X secreted phospholipase A2 (GX-sPLA2)-induced airway inflammation and hyperresponsiveness in a mouse asthma model by a selective GX-sPLA2 inhibitor". Journal of biological chemistry, 2011, 286(32):28049-55.
Oslund et al, "Highly specific and broadly potent inhibitors of mammalian secreted phospholipases A2", Journal of medicinal chemistry, 2008, 51(15):4708-17.
Saiga et al, "Group X secretory phospholipase A2 can induce arachidonic acid release and eicosanoid production without activation of cytosolic phospholipase A2 alpha" Prostaglandins and other lipid mediators, 2005, 75(1-4):79-89.
Gora et al,"Molecular and functional characterization of polymorphisms in the secreted phospholipase A2 group X gene: relevance to coronary artery disease", Journal of molecular medicine, 2009, 87(7):723-33.
European Search report (ESR) of EP2641916 ; Jul. 13, 2012.
International Search Report (ISR) of WO2013/139968; Jun. 11, 2013.

\* cited by examiner

ANTI-SPLA2-IIA ANTIBODIES AND USES THEREOF

CROSS-REFERENCE TO RELATED APPLICATIONS

This application is a national phase application under 35 U.S.C. §371 of International Application No. PCT/EP2013/056085 filed 22 Mar. 2013, which claims priority to European Patent Application No. 12161036.4 filed 23 Mar. 2012. The entire contents of each of the above-referenced disclosures is specifically incorporated herein by reference without disclaimer.

FIELD OF INVENTION

The present invention relates to novel antibodies against human group IIA secreted phospholipase A2 (sPLA2-IIA) and uses thereof in diagnostic and treatment methods.

BACKGROUND OF INVENTION

Secreted phospholipases A2 (sPLA2) form a family of structurally related enzymes that catalyze the hydrolysis of the sn-2 fatty acyl bond of phospholipids to release free fatty acids and lysophospholipids. By catalyzing this reaction, sPLA2 enzymes play a key role in various biological processes including homeostasis of cellular membranes, lipid digestion, host defense, signal transduction, and production of lipid mediators such as eicosanoids and lysophospholipid derivatives (Valentin et al. 2000, Bioch. Biophys. Act. 59-70; Lambeau, G., and Gelb, M. H. 2008, Annu. Rev. Biochem. 77, 495-520). This family comprises eleven members/isoforms named sPLA2-IB, sPLA2-IIA, sPLA2-IIC, sPLA2-IID, sPLA2-IIE, sPLA2-IIF, sPLA2-III, sPLA2-V, sPLA2-X, sPLA2-XIIA and sPLA2-XIIB.

Quantification of specific isoforms at the protein level has proven to be difficult because of similar enzymatic activities and the absence of isoform-specific sPLA2 antibodies.

Nevalainen et al. (Biochimica et Biophysica Acta 1733 (2005) 210-223) developed an antibody against sPLA2-IIA for use in a time-resolved fluoroimmunoassay (TR-FIA). This polyclonal antibody was obtained by immunizing rabbits with recombinant human sPLA2-IIA protein. The analytical sensitivity of the TR-FIA was described as 1 ng/ml.

Cayman chemical provides a monoclonal antibody under reference SCACC353. According to the experimental results obtained by the inventors, the SCACC353 antibody has a Kd for binding human sPLA2-IIA of about 1 nM (see Examples).

There is currently a need for antibodies against sPLA2-IIA that allow a more accurate and sensitive detection of sPLA2-IIA in biological sample such as serum sample.

SUMMARY

The present invention thus relates to an isolated antibody against human sPLA2-IIA, wherein said antibody has a Kd for binding to human sPLA2-IIA less than $9.10^{-10}$ M.

In one embodiment of the invention, the variable region of the heavy chain comprises at least one of the following CDRs:

VH-CDR1: GYTFTS; (SEQ ID NO: 1)

VH-CDR2: WIFPGDGSTE; (SEQ ID NO: 2) and

VH-CDR3: WGITAFPLFDY, (SEQ ID NO: 3)

or any CDR having an amino acid sequence that shares at least 60% of identity with SEQ ID NO: 1-3, or the variable region of the light chain comprises at least one of the following CDRs:

VL-CDR1: RASESVDYDGDSYMN; (SEQ ID NO: 4)

VL-CDR2: AASNLES; (SEQ ID NO: 5) and

VL-CDR3: LQSNEAPWT, (SEQ ID NO: 6)

or any CDR having an amino acid sequence that shares at least 60% of identity with SEQ ID NO: 4-6.

In one embodiment of the invention, the variable region of the heavy chain comprises at least one of the CDRs as defined herein above and the variable region of the light chain comprises at least one of the CDRs as defined herein above.

In one embodiment of the invention, the variable region of the heavy chain comprises the following CDRs: GYTFTS (SEQ ID NO: 1), WIFPGDGSTE (SEQ ID NO: 2) and WGITAFPLFDY (SEQ ID NO: 3) and the variable region of the light chain comprises the following CDRs: RASESVDYDGDSYMN (SEQ ID NO: 4), AASNLES (SEQ ID NO: 5) and LQSNEAPWT (SEQ ID NO: 6) or any CDR having an amino acid sequence that shares at least 60% of identity with said SEQ ID NO: 1-6.

In one embodiment of the invention, the amino acid sequence encoding the heavy chain variable region is SEQ ID NO: 13 and the amino acid sequence encoding the light variable region is SEQ ID NO: 14, or any sequence having an amino acid sequence that shares at least 60% of identity with said SEQ ID NO: 13-14.

The present invention also relates to a composition comprising the antibody against human sPLA2-IIA as described herein above.

The present invention also relates to the antibody against human sPLA2-IIA as described herein above for treating a sPLA2-IIA-related condition.

The present invention also relates to the antibody against human sPLA2-IIA as described herein above for detecting sPLA2-IIA in a biological sample.

The present invention also relates to an in vitro diagnostic or prognostic assay for determining the presence of sPLA2-IIA in a biological sample using the antibody against human sPLA2-IIA of the invention.

In one embodiment of the invention, the assay is a sandwich ELISA using the antibody as herein above described as coating antibody and as revealing antibody an antibody wherein:

the variable region of the heavy chain comprises at least one of the following CDRs:

```
                                                 (SEQ ID NO: 7)
VH-CDR1: GFTFSS;

(SEQ ID NO: 8)
VH-CDR2: AINSNGGSTY;
and (SEQ ID NO: 9)
VH-CDR3: QGYGNFFDY,
``` or any CDR having an amino acid sequence that shares at least 60% of identity with SEQ ID NO: 7-9, or the variable region of the light chain comprises at least one of the following CDRs:

```
                                                 (SEQ ID NO: 10)
VL-CDR1: RSSQSIVHSNGNTYLY;

(SEQ ID NO: 11)
VL-CDR2: RVSNRFS;
and (SEQ ID NO: 12)
VL-CDR3: FQGTHVPRT,
``` or any CDR having an amino acid sequence that shares at least 60% of identity with SEQ ID NO: 10-12.

In one embodiment of the invention, the variable region of the heavy chain of the revealing antibody comprises at least one of the CDRs as defined herein above (SEQ ID NO: 7 to SEQ ID NO: 9) and the variable region of the light chain of the revealing antibody comprises at least one of the CDRs as defined herein above (SEQ ID NO: 10 to SEQ ID NO: 12).

In one embodiment of the invention, the variable region of the heavy chain of the revealing antibody comprises the following CDRs: GFTFSS (SEQ ID NO: 7), AINSNGGSTY (SEQ ID NO: 8) and QGYGNFFDY (SEQ ID NO: 9) and the variable region of the light chain of the revealing antibody comprises the following CDRs: RSSQSIVH-SNGNTYLY (SEQ ID NO: 10), RVSNRFS (SEQ ID NO: 11) and FQGTHVPRT (SEQ ID NO: 12) or any CDR having an amino acid sequence that shares at least 60% of identity with said SEQ ID NO: 7-12.

In one embodiment of the invention, the amino acid sequence encoding the heavy chain variable region of the revealing antibody is SEQ ID NO: 15 and the amino acid sequence encoding the light variable region of the revealing antibody is SEQ ID NO: 16, or any sequence having an amino acid sequence that shares at least 60% of identity with said SEQ ID NO: 15-16.

The present invention also relates to a kit comprising at least one antibody against human sPLA2-IIA of the invention.

In one embodiment, the kit comprises an antibody of the invention and a revealing antibody of the invention.

The present invention also relates to an expression vector comprising at least one of SEQ ID NO: 17, SEQ ID NO: 18, SEQ ID NO: 19, and SEQ ID NO: 20 or any sequence having a nucleic acid sequence that shares at least 60% of identity with said SEQ ID NO: 17-20.

The present invention also relates to the hybridoma cell lines producing an antibody against human sPLA2-IIA registered under CNCM 1-4587 and CNCM 1-4588.

DETAILED DESCRIPTION

The inventors developed new antibodies against human sPLA2-IIA that show a higher affinity for sPLA2-IIA than existing antibodies and allow a more accurate and sensitive detection of sPLA2-IIA in a biological sample as shown in the Examples.

In addition, the inventors provided monoclonal antibodies against human sPLA2-IIA, which present the advantage (i) to be more specific than polyclonal antibodies, and (ii) due to the reproducibility of the results linked to their monoclonal nature, to allow an industrial use of said antibodies.

DEFINITIONS sPLA2-IIA is an isoform of the sPLA2 family. The complete amino acid sequence of the human sPLA2-IIA protein (SEQ ID NO: 21) (GenBank Accession # NP_000291) is:

```
MKTLLLLAVIMIFGLLQAHG (signal peptide)

NLVNFHRMIKLTTGKEAALSYGFYGCHCGVGGRGSPKDATDRCCVTHDCC
YKRLEKRGCGTKFLSYKFSNSGSRITCAKQDSCRSQLCECDKAAATCFAR
NKTTYNKKYQYYSNKHCRGSTPRC (mature protein).
```

In one embodiment, sPLA2-IIA is a mutant sPLA2-IIA, preferably the N1A sPLA2-IIA mutant, having the sequence SEQ ID NO: 22:

```
MKTLLLLAVIMIFGLLQAHG (signal peptide)

ALVNFHRMIKLTTGKEAALSYGFYGCHCGVGGRGSPKDATDRCCVTHDCC
YKRLEKRGCGTKFLSYKFSNSGSRITCAKQDSCRSQLCECDKAAATCFAR
NKTTYNKKYQYYSNKHCRGSTPRC (mature protein).
```

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. The L chain from any vertebrate species can be assigned to one of two clearly distinct types, called kappa ([kappa]) and lambda ([lambda]), based on the amino acid sequences of their constant domains (CL). Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ([alpha]), delta ([delta]), epsilon ([epsilon]), gamma ([gamma]) and mu ([mu]), respectively. The [gamma] and [alpha] classes are further divided into subclasses on the basis of relatively minor differences in CH sequence and function, e.g., humans express the following subclasses: IgG1, IgG2, IgG3, IgG4, IgA1, and IgA2. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the [alpha] and [gamma] chains and four CH domains for [mu] and [epsilon]isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. An IgM antibody consists of five of the basic heterotetramer units along with an additional polypeptide called a J chain, and therefore, contains ten antigen binding sites, while secreted IgA antibodies can polymerize to form polyvalent assemblages comprising 2-5 of the basic 4-chain units along with J chain. In the case of IgGs, the 4-chain unit is generally about 150,000 Daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a [beta]-sheet configuration, connected by three hypervariable regions, which form loops connecting, and in some cases forming part of, the [beta]-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with AHo (Honneger, A. and Plunkthun, A. J. Mol. Biol. 309:657-670 (2001)).

The term "monoclonal antibody" as used herein refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments. The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc[epsilon]RI. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

A "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference). Accordingly, a "primatized" antibody refers to an antibody in which the constant and variable framework region of one or more primate immunoglobulins is fused with the binding region, e.g. the CDR, of a non-primate immunoglobulin.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Holliger et al., Proc. Natl. Acad. Sci. USA, 90:6444-6448 (1993).

As used herein, an antibody is said to be "immunospecific," "specific for" or to "specifically bind" an antigen if it reacts at a detectable level with the antigen, preferably with an affinity constant, Ka, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$, or greater than or equal to $10^9$ $M^{-1}$, or greater than or equal to $10^{10}$ M. Affinity of an antibody for its cognate antigen is also commonly expressed as a dissociation constant Kd, and in certain embodiments, an antibody specifically binds to antigen if it binds with a Kd of less than or equal to $10^{-4}$ M, less than or equal to about $10^{-5}$ M, less than or equal to about $10^{-6}$ M, less than or equal to $10^{-7}$ M, or less than or equal to $10^{-8}$ M, or less than or equal to $5.10^{-9}$ M, or less than or equal to $10^{-9}$ M, or less than or equal to $5.10^{-10}$ M, or less than or equal to $10^{-10}$ M. Affinities of antibodies can be readily determined using conventional techniques, for example, those described by Scatchard et al. (Ann. N.Y. Acad. Sci. USA 51:660 (1949)). Binding properties of an antibody to antigens, cells or tissues thereof may generally be determined and assessed using immunodetection methods including, for example, immunofluorescence-based assays, such as immunohistochemistry (IHC) and/or fluorescence-activated cell sorting (FACS).

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man. The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen. An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means. A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art. A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence. For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences of the disclosed compositions, or corresponding DNA sequences that encode said peptides without appreciable loss of their biological utility or activity. In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

A "mammal" as used herein, refers to any mammal, including humans, domestic and farm animals, and zoo, sports, or pet animals, such as dogs, cats, cattle, horses, sheep, pigs, goats, rabbits, etc. Preferably, the mammal is human. In one embodiment, the mammal is a male. In another embodiment, the mammal is a female.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of pathogenic cells; reduction in the percent of total cells that are pathogenic; and/or relief to some extent, one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal.

THE INVENTION

The present invention relates to isolated antibodies against sPLA2-IIA.

Antibodies anti-sPLA2-IIA

One object of the invention is an antibody against human sPLA2-IIA, wherein said antibody has a Kd for binding to human sPLA2-IIA less than $9.10^{-10}$ M, preferably less than $8.10^{-10}$ M, $7.10^{-10}$ M, $6.10^{-10}$ M, $5.10^{-10}$ M, $4.10^{-10}$ M, more preferably less than $3.10^{-10}$ M and even more preferably less than $2.10^{-10}$ M.

The Kd may be determined in the conditions of Test A:

Microplate wells are coated with 50 ng of recombinant human sPLA2-IIA in PBS pH 7.5, overnight at room temperature. Sample wells are then washed three times with PBS containing 0.05% Tween 20. After final washing, sample wells are treated with blocking solution containing 1% bovine serum albumin (BSA) in PBS buffer for 60 min at room temperature. Following washing with PBS containing 0.05% Tween 20, increasing amounts (0.1 ng/mL up to 10 µg/mL) of mAb directed against human PLA2-IIA are added to antigen-coated wells, and incubated for 120 min at room temperature. Following washing with PBS containing 0.05% Tween 20, the binding of mAb is detected by treatment with HRP-conjugated polyclonal goat anti-mouse IgG (Abcam ab7068) for 60 min at room temperature. TMB is added, reaction is stopped by adding HCl and absorbance at 450 nm is determined. Data are fitted with a one-site saturation model and the relative Kd values are estimated from the model.

One object of the invention is an antibody against human sPLA2-IIA wherein the variable region of the heavy chain comprises at least one of the followings CDRs:

```
VH-CDR1:
                                      (SEQ ID NO: 1)
GYTFTS
or
                                      (SEQ ID NO: 7)
GFTFSS;

VH-CDR2:
                                      (SEQ ID NO: 2)
WIFPGDGSTE
or
                                      (SEQ ID NO: 8)
AINSNGGSTY;
and VH-CDR3:
                                      (SEQ ID NO: 3)
WGITAFPLFDY
or
                                      (SEQ ID NO: 9)
QGYGNFFDY.
```

CDR numbering and definition are according to the Chothia definition.

Another object of the invention is an antibody against human sPLA2-IIA wherein the variable region of the light chain comprises at least one of the followings CDRs:

VL-CDR1: RASESVDYDGDSYMN (SEQ ID NO: 4)
or
RSSQSIVHSNGNTYLY; (SEQ ID NO: 10)

VL-CDR2: AASNLES (SEQ ID NO: 5)
or
RVSNRFS; (SEQ ID NO: 11)
and

VL-CDR3: LQSNEAPWT (SEQ ID NO: 6)
or
FQGTHVPRT. (SEQ ID NO: 12)

In one embodiment of the invention, the antibody anti-sPLA2-IIA comprises in its heavy chain one VH-CDR1 among GYTFTS (SEQ ID NO: 1) or GFTFSS (SEQ ID NO: 7), one VH-CDR2 among WIFPGDGSTE (SEQ ID NO: 2) or AINSNGGSTY (SEQ ID NO: 8) and one VH-CDR3 among WGITAFPLFDY (SEQ ID NO: 3) or QGYGNFFDY (SEQ ID NO: 9).

In another embodiment of the invention, the antibody anti-sPLA2-IIA comprises in its light chain one VL-CDR1 among RASESVDYDGDSYMN (SEQ ID NO: 4) or RSSQSIVHSNGNTYLY (SEQ ID NO: 10), one VL-CDR2 among AASNLES (SEQ ID NO: 5) or RVSNRFS (SEQ ID NO: 11) and one VL-CDR3 among LQSNEAPWT (SEQ ID NO: 6) or FQGTHVPRT (SEQ ID NO: 12).

In another embodiment of the invention, the antibody anti-sPLA2-IIA comprises in its heavy chain the 3 CDRs SEQ ID NO: 1, SEQ ID NO: 2 and SEQ ID NO: 3.

In another embodiment of the invention, the antibody anti-sPLA2-IIA comprises in its heavy chain the 3 CDRs SEQ ID NO: 7, SEQ ID NO: 8 and SEQ ID NO: 9.

In another embodiment of the invention, the antibody anti-sPLA2-IIA comprises in its light chain the 3 CDRs SEQ ID NO: 4, SEQ ID NO: 5 and SEQ ID NO: 6.

In another embodiment of the invention, the antibody anti-sPLA2-IIA comprises in its light chain the 3 CDRs SEQ ID NO: 10, SEQ ID NO: 11 and SEQ ID NO: 12.

According to the invention, any of the CDRs 1, 2 and 3 of the heavy and light chains may be characterized as having an amino acid sequence that shares at least 60%, 70%, 75%, 80%, 90%, 95%, 96%, 97%, 98%, 99% of identity with the particular CDR or sets of CDRs listed in the corresponding SEQ ID NO.

In another embodiment of the invention, the antibody anti-sPLA2-IIA is selected from the group consisting of:
  an antibody having (i) the heavy chain CDR 1, 2 and 3 (VH-CDR1, VH-CDR2, VH-CDR3) amino acid sequences as shown in SEQ ID NO: 1, 2 and 3 and (ii) the light chain CDR 1, 2 and 3 (VL-CDR1, VL-CDR2, VL-CDR3) amino acid sequences as shown in SEQ ID NO: 4, 5 and 6 respectively;
  an antibody having (i) the heavy chain CDR 1, 2 and 3 (VH-CDR1, VH-CDR2, VH-CDR3) amino acid sequences as shown in SEQ ID NO: 7, 8 and 9 and (ii) the light chain CDR 1, 2 and 3 (VL-CDR1, VL-CDR2, VL-CDR3) amino acid sequences as shown in SEQ ID NO: 10, 11 and 12 respectively;
optionally wherein one, two, three or more of the amino acids in any of said sequences may be substituted by a different amino acid.

In another embodiment of the invention, the antibody anti-sPLA2-IIA (6G2 antibody) comprises the heavy chain variable region of sequence SEQ ID NO: 13 and the light chain variable region of sequence SEQ ID NO: 14.

(SEQ ID NO: 13)
QVQLQQSGAELVKPGASVKLSCKASGYTFTSYDINWVRQRPEQGLEWIGW
IFPGDGSTEYNEKFKGKATLTTDKSSSTAYMQLSRLTSEDSAVYFCARWG
ITAFPLFDYWGQGTALTVSS (SEQ ID NO: 14)
DIVLTQSPASLAVSLGQRATISCRASESVDYDGDSYMNWYQQKPGQPPKL
LIYAASNLESGIPARFSGSGSGTDFTLNIHPVEEEDAATYYCLQSNEAPW
TFGGGTKLEIKR

In another embodiment of the invention, the antibody anti-sPLA2-IIA (9C8 antibody) comprises the heavy chain variable region of sequence SEQ ID NO: 15 and the light chain variable region of sequence SEQ ID NO: 16.

(SEQ ID NO: 15)
DVELVESGGGLVKLGGSLKLSCAASGFTFSSYYMSWVRQTPEKRLELVAA
INSNGGSTYYPDTVKGRFTISRDNAKNTLYLQMSSLKSEDTALYYCARQG
YGNFFDYWGQGTTLTVSS (SEQ ID NO: 16)
DVVMTQTPLSLPVSLGDQASISCRSSQSIVHSNGNTYLYWYLQKPGQSPK
LLIYRVSNRFSGVPDRFSGSGSGTDFTLKISRVEAEDMGVYYCFQGTHVP
RTFGGGTNLEIKR

According to the invention, one, two, three or more of the amino acids of the heavy chain or light chain variable regions may be substituted by a different amino acid.

According to the invention, the heavy chain variable region encompasses sequences that have 60%, 70%, 75%, 80%, 90%, 95%, 96%, 97%, 98%, 99% of identity with SEQ ID NO: 13 or 15.

According to the invention, the light chain variable region encompasses sequences that have 60%, 70%, 75%, 80%, 90%, 95%, 96%, 97%, 98%, 99% of identity with SEQ ID NO: 14 or 16.

In any of the antibodies of the invention, e.g. 6G2 and 9C8, the specified variable region and CDR sequences may comprise conservative sequence modifications. Conservative sequence modifications refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

In one embodiment, the invention also provides an antibody that binds essentially the same epitope as 6G2 or 9C8 antibodies. In the present invention, an antibody that binds essentially the same epitope as 6G2 or 9C8 antibodies will be referred as a 6G2-like or 9C8-like antibody, respectively.

Another object of the invention is an isolated nucleic sequence encoding the heavy chain variable region of sequence SEQ ID NO: 13. Preferably, said nucleic sequence is SEQ ID NO: 17 (CAG GTT CAG CTG CAG CAG TCT GGA GCT GAA CTG GTA AAG CCT GGG GCT TCA GTG AAG TTG TCC TGC AAG GCT TCT GGC TAC ACC TTC ACA AGC TAT GAT ATA AAC TGG GTG AGG CAG AGG CCT GAA CAG GGA CTT GAG TGG ATT GGA TGG ATT TTT CCT GGA GAT GGT AGT ACT GAG TAC AAT GAG AAG TTC AAG GGC AAG GCC ACA CTG ACT ACA GAC AAA TCC TCC ACA GCC TAC ATG CAG CTC AGC AGG CTG ACA TCT GAG GAC TCT GCT GTC TAT TTC TGT GCA AGG TGG GGT ATT ACG GCT TTC CCC CTT TTT GAC TAC TGG GGC CAA GGC ACC GCT CTC ACA GTC TCC TCA).

Another object of the invention is an isolated nucleic sequence encoding the light chain variable region of sequence SEQ ID NO: 14. Preferably, said nucleic sequence is SEQ ID NO: 18 (GAC ATT GTG CTG ACC CAA TCT CCA GCT TCT TTG GCT GTG TCT CTA GGG CAG AGG GCC ACC ATC TCC TGC AGA GCC AGC GAA AGT GTT GAT TAT GAT GGC GAT AGT TAT ATG AAC TGG TAC CAA CAG AAA CCA GGA CAG CCA CCG AAA CTC CTC ATC TAT GCT GCA TCC AAT CTA GAA TCT GGG ATC CCT GCC AGG TTT AGT GGC AGT GGG TCT GGG ACA GAC TTC ACC CTC AAC ATT CAT CCT GTG GAG GAG GAG GAT GCT GCA ACC TAT TAC TGT CTG CAA AGT AAT GAG GCT CCG TGG ACG TTC GGT GGA GGC ACC AAG CTG GAA ATC AAA CGG).

Another object of the invention is an isolated nucleic sequence encoding the heavy chain variable region of sequence SEQ ID NO: 15. Preferably, said nucleic sequence is SEQ ID NO: 19 (GAC GTG GAG CTC GTG GAG TCT GGG GGA GGC TTA GTG AAG CTT GGA GGG TCC CTA AAA CTC TCC TGT GCA GCC TCT GGA TTC ACT TTC AGT AGC TAT TAC ATG TCT TGG GTT CGC CAG ACT CCA GAG AAG AGG CTG GAG TTG GTC GCA GCC ATT AAT AGT AAT GGT GGT AGC ACC TAC TAT CCA GAC ACT GTG AAG GGC CGA TTC ACC ATC TCC AGA GAC AAT GCC AAG AAC ACC CTG TAC CTG CAA ATG AGC AGT CTG AAG TCT GAG GAC ACA GCC TTG TAT TAC TGT GCA AGA CAG GGG TAT GGT AAC TTC TTT GAC TAC TGG GGC CAA GGC ACC ACT CTC ACA GTC TCC TCA).

Another object of the invention is an isolated nucleic sequence encoding the light chain variable region of sequence SEQ ID NO: 16. Preferably, said nucleic sequence is SEQ ID NO: 20 (GAT GTT GTG ATG ACC CAA ACT CCA CTC TCC CTG CCT GTC AGT CTT GGA GAT CAA GCC TCC ATC TCT TGT AGA TCT AGT CAG AGC ATT GTA CAC AGT AAT GGA AAC ACC TAT TTA TAT TGG TAC CTG CAG AAA CCA GGC CAG TCT CCA AAG CTC CTG ATC TAC AGG GTT TCC AAC CGA TTT TCT GGG GTC CCA GAC AGG TTC AGT GGC AGT GGA TCA GGG ACA GAT TTC ACA CTC AAG ATC AGC AGA GTG GAG GCT GAG GAT ATG GGA GTT TAT TAC TGC TTT CAA GGT ACA CAT GTT CCT CGG ACG TTC GGT GGA GGC ACC AAC TTG GAA ATC AAA CGG).

Another object of the invention is an expression vector comprising the nucleic sequences encoding the antibody anti-sPLA2-IIA of the invention. In one embodiment, the expression vector of the invention comprises at least one of SEQ ID NO: 17, SEQ ID NO: 18, SEQ ID NO: 19 and SEQ ID NO: 20 or any sequence having a nucleic acid sequence that shares at least 60%, 70%, 75%, 80%, 90%, 95%, 96%, 97%, 98%, 99% of identity with said SEQ ID NO: 17-20.

Another object of the invention is an isolated host cell comprising said vector. Said host cell may be used for the recombinant production of the antibodies of the invention.

Another object of the invention is a hybridoma cell line which produce said antibody of the invention.

The preferred hybridoma cell lines according to the invention were deposited with the Collection Nationale de Culture de Microorganismes (CNCM), Institut Pasteur, 25 rue du Docteur Roux, 75014 Paris:

| Cell line | Deposition No. | Date of deposit |
| --- | --- | --- |
| 6G2 hybridoma | CNCM I-4588 | Dec. 13, 2011 |
| 9C8 hybridoma | CNCM I-4587 | Dec. 13, 2011 |

In one embodiment of the invention, the antibody is a monoclonal antibody.

Fragments and derivatives of antibodies of this invention (which are encompassed by the term "antibody" or "antibodies" as used in this application, unless otherwise stated or clearly contradicted by context), preferably a 6G2-like or 9C8-like antibody, can be produced by techniques that are known in the art. "Fragments" comprise a portion of the intact antibody, generally the antigen binding site or variable region. Examples of antibody fragments include Fab, Fab', Fab'-SH, F (ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Fragments of the present antibodies can be obtained using standard methods. For instance, Fab or F (ab')2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, Cytokines 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of the invention, preferably a 6G2-like or 9C8-like antibody, may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention, preferably a 6G2-like or 9C8-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a 6G2-like or 9C8-like antibody, is humanized. "Humanized" forms of antibodies according to this invention are specific chimeric immunoglobulins, immunoglobulin chains or fragments thereof (such as Fv, Fab, Fab', F (ab')2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence that is closest to the mouse sequence is then accepted as the human framework (FR) for the humanized antibody (Sims et al., J. Immunol. 151, pp. 2296 (1993); Chothia and Lesk, J. Mol. Biol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et J. Immunol., 51 (1993)). It is further important that antibodies be humanized with retention of high affinity for sPLA2-IIA and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, CDR residues can be selected and combined from the consensus and import sequences so that the desired antibody characteristic, such as increased affinity for the target antigen (s), is achieved. In general, the CDR residues are directly and most substantially involved in influencing antigen binding. Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et Nature 362 (1993) 255), or by selection of antibody repertoires using phage display methods. Such techniques are known to the skilled person and can be implemented starting from monoclonal antibodies as disclosed in the present application.

The antibodies of the present invention, preferably a 6G2-like or 9C8-like antibody, may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A., pp. 6851 (1984)).

Compositions and Uses in Therapy

One object of the invention is a composition comprising at least one of the antibody anti-sPLA2-IIA of the invention, preferably 6G2 or 9C8 antibody.

Another object of the invention is a pharmaceutical composition comprising at least one of the antibody anti-sPLA2-IIA of the invention as described here above, preferably 6G2 or 9C8 antibody and a pharmaceutically acceptable carrier.

Another object of the invention is the antibody anti-sPLA2-IIA of the invention for or for use in modulating (inhibiting or activating) sPLA2-IIA activity, or for or for use in treating a sPLA2-IIA-related condition.

Another object of the invention is a method for modulating (inhibiting or activating) sPLA2-IIA activity in a subject in need thereof, comprising administering to the subject an effective amount of the antibody anti-sPLA2-IIA of the invention.

Another object of the invention is a method for treating sPLA2-IIA-related condition in a subject in need thereof, comprising administering to the subject an effective amount of the antibody anti-sPLA2-IIA of the invention.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for intravenous (IV) administration in 9.0 mg/mL sodium chloride, 7.35 mg/mL sodium citrate dihydrate, 0.7 ing/mL polysorbate 80, and Sterile Water for Injection. The pH is adjusted to 6.5. It will be appreciated that these schedules are exemplary and that an optimal schedule and regimen can be adapted taking into account the affinity and tolerability of the particular antibody in the pharmaceutical composition that must be determined in clinical trials.

Diseases or conditions where the methods of the invention can be used include all diseases where modulation (inhibition or activation) of sPLA2-IIA can be beneficial.

Said sPLA2-IIA-related condition includes, but is not limited to, inflammatory diseases, cancer (such as, for example, prostate cancer), sepsis, infectious diseases, severe surgery or other injuries with severe wound areas, diabetic shock, acute liver failure, pancreatitis, neurodegenerative diseases, autoimmune diseases e.g. Systemic Lupus Erythematosus (SLE), osteoarthritis, rheumatoid arthritis, multiple sclerosis, myasthenia gravis, Graves' disease, psoriasis vulgaris, dilated cardiomyopathy, diabetes mellitus, Bechterew, inflammatory bile disease, ulcerative colitis, Crohn's disease, idiopathic thrombocytopenia purpura (ITP), plastic anemia, idiopathic dilated cardiomyopathy (IDM), autoimmune thyroiditis, Goodpastures' disease, arterial and venous chronic inflammation.

In another embodiment, said sPLA2-IIA-related condition is a cardiovascular disease and/or a cardiovascular event. Said cardiovascular disease and/or cardiovascular event includes, but is not limited to, ischemic event, ischemia, heart attack, Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and any acute ischemic cardiovascular event.

Compositions and Uses in Diagnostics and Prognostics

Another object of the invention is the use of at least one of the antibodies anti-sPLA2-IIA of the invention for detecting sPLA2-IIA in a sample, preferably in a biological sample, in vitro or in vivo.

Another object of the invention is the use of at least one of the antibodies anti-sPLA2-IIA of the invention for screening in vitro or in vivo molecules inhibiting or activating sPLA2-IIA.

Examples of assays in which the antibody of the invention may be used, include, but are not limited to, ELISA, sandwich ELISA, RIA, FACS, tissue immunohistochemistry, Western-blot, and immunoprecipitation.

Another object of the invention is a method for detecting sPLA2-IIA in a sample, comprising contacting the sample with an anti-sPLA2-IIA antibody of the invention and detecting the anti-sPLA2-IIA antibody bound to sPLA2-IIA, thereby indicating the presence of sPLA2-IIA in the sample.

In one embodiment of the invention, the sample is a biological sample. Examples of biological samples include, but are not limited to, bodily fluids, preferably blood, more preferably blood serum, plasma, synovial fluid, bronchioalveolar lavage fluid, sputum, lymph, ascitic fluids, urine, amniotic fluid, peritoneal fluid, cerebrospinal fluid, pleural fluid, pericardial fluid, and alveolar macrophages, tissue lysates and extracts prepared from diseased tissues.

In one embodiment of the invention, the term "sample" is intended to mean a sample taken from an individual prior to any analysis.

In one embodiment of the invention, the anti-sPLA2-IIA antibody is directly labeled with a detectable label and may be detected directly. In another embodiment, the anti-sPLA2-IIA antibody is unlabeled (and is referred as the first/primary antibody) and a secondary antibody or other molecule that can bind the anti-sPLA2-IIA antibody is labeled. As it is well known in the art, a secondary antibody is chosen to be able to specifically bind the specific species and class of the primary antibody.

The presence of anti-sPLA2-IIA/sPLA2-IIA complex in the sample can be detected and measured by detecting the presence of the labeled secondary antibody. For example, after washing away unbound secondary antibody from a well comprising the primary antibody/antigen complex or from a membrane (such as a nitrocellulose or nylon membrane) comprising the complex, the bound secondary antibody can be developed and detected based on chemiluminescence of the label for example.

Labels for the anti-sPLA2-IIA antibody or the secondary antibody include, but are not limited to, various enzymes, prosthetic groups, fluorescent materials, luminescent materials, magnetic agents and radioactive materials. Examples of such enzymes include horseradish peroxidase, alkaline phosphatase, beta-galactosidase or acetylcholinesterase; examples of prosthetic group complexes include streptavidin/biotin and avidin/biotin; examples of fluorescent materials include umbelliferone, fluorescein, fluorescein isothiocyanate, rhodamine, dichlorotriazinylamine fluorescein, dansyne chloride or phycoerythrin; examples of luminescent material include luminal; examples of magnetic agents include gadolinium; and examples of suitable radioactive material include $^{125}$I, $^{131}$I, $^{35}$S or $^3$H.

Another object of the invention is the use of the anti-sPLA2-IIA antibodies of the invention for in vitro diagnostic assays by determining the level of sPLA2-IIA in subject samples. Such assays may be useful for diagnosing diseases associated with over-expression of sPLA2-IIA.

Another object of the invention is the use of the anti-sPLA2-IIA antibodies of the invention for in vitro determining the risk of a subject to develop sPLA2-IIA associated diseases.

In one embodiment, said disease is an inflammatory condition.

Said sPLA2-IIA-related condition includes, but is not limited to, inflammatory diseases, cancer (such as, for example, prostate cancer), sepsis, infectious diseases, severe surgery or other injuries with severe wound areas, diabetic shock, acute liver failure, pancreatitis, neurodegenerative diseases, autoimmune diseases e.g. SLE, osteoarthritis, rheumatoid arthritis, multiple sclerosis, myasthenia gravis, Graves' disease, psoriasis vulgaris, dilated cardiomyopathy, diabetes mellitus, Bechterew, inflammatory bile disease, ulcerative colitis, Crohn's disease, idiopathic thrombocytopenia purpura (ITP), plastic anemia, idiopathic dilated cardiomyopathy (IDM), autoimmune thyroiditis, Goodpastures' disease, arterial and venous chronic inflammation.

In another embodiment, said sPLA2-IIA-related condition is a cardiovascular disease and/or a cardiovascular event. Said cardiovascular disease and/or cardiovascular event includes, but is not limited to, ischemic event, ischemia, heart attack, Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and any acute ischemic cardiovascular event.

Another object of the invention is the use of the anti-sPLA2-IIA antibodies of the invention for in vitro determining the risk of a subject to develop a sPLA2-IIA-related condition, preferably a cardiovascular disease and/or a cardiovascular event. Said cardiovascular disease and/or cardiovascular event includes, but is not limited to, ischemic event, ischemia, heart attack, Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and any acute ischemic cardiovascular event.

The concentration or quantity of sPLA2-IIA present in a subject sample can be determined using a method that specifically determines the amount of sPLA2-IIA present. Such a method includes an ELISA method in which, for example, antibodies of the invention may be conventionally immobilized on an insoluble matrix such as a polymer matrix. Alternatively, a sandwich ELISA method can be used as described here above. Immunohistochemistry staining assays may also be used.

Using a population of samples that provides statistically significant results for each stage of progression or therapy, a range of concentrations of sPLA2-IIA that may be considered characteristic of each stage of disease can be designated.

In one embodiment, a sample of blood or serum is taken from a subject and the concentration of sPLA2-IIA present in the sample is determined to evaluate the stage of the disease in the subject under study, or to characterize the response of the subject in the course of therapy. The concentration so obtained is used to identify in which range of concentrations the value falls. The range so identified correlates with a stage of disease progression or a stage of therapy identified in the various population of diagnosed subjects, thereby providing a stage in the subject under study.

One object of the invention is a sandwich ELISA method that may be used for comparing the level of bound sPLA2-IIA protein in a sample obtained from a subject to a threshold level to determine if the subject has a sPLA2-IIA-related condition.

As used herein, "threshold level" refers to a level of sPLA2-IIA expression above which a subject sample is deemed "positive" and below which the sample is classified as "negative" for the disease. A threshold expression level for a particular biomarker (e.g., sPLA2-IIA) may be based on compilations of data from healthy subject samples (i.e., a healthy subject population). For example, the threshold expression level may be established as the mean sPLA2-IIA expression level plus two times the standard deviation, based on analysis of samples from healthy subjects. One of skill in the art will appreciate that a variety of statistical and mathematical methods for establishing the threshold level of expression are known in the art.

One of skill in the art will further recognize that the capture and revelation antibodies can be contacted with the sample sequentially, as described above, or simultaneously. Furthermore, the revelation antibody can be incubated with the sample first, prior to contacting the sample with the immobilized capture antibody. When the anti-sPLA2-IIA monoclonal antibodies of the present invention are used in the sandwich ELISA methods disclosed herein, either the 6G2 or 9C8 antibody may be used as the capture or revelation antibody. In one particular embodiment, the capture antibody is monoclonal antibody 6G2 and the revelation antibody is the 9C8 antibody, more particularly a HRP-labeled 9C8 antibody. The antibodies of the invention may be used in any assay format to detect sPLA2-IIA, including but not limited to multiplex bead-based assays.

With respect to the sandwich ELISA format described above in which two antibodies for the same biomarker (i.e., sPLA2-IIA) are used, the capture and revelation antibodies should have distinct antigenic sites. By "distinct antigenic site" is intended that the antibodies are specific for different sites on the biomarker protein of interest (i.e., sPLA2-IIA) such that binding of one antibody does not significantly interfere with binding of the other antibody to the biomarker protein. Antibodies that are not complementary are not suitable for use in the sandwich ELISA methods described above.

Another object of the invention is a kit comprising at least one anti-sPLA2-IIA monoclonal antibody of the invention. By "kit" is intended any manufacture (e.g., a package or a container) comprising at least one reagent, i.e., an antibody, for specifically detecting the expression of sPLA2-IIA. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

Kits for performing the sandwich ELISA methods of the invention generally comprise a capture antibody, optionally immobilized on a solid support (e.g., a microtiter plate), and a revelation antibody coupled with a detectable substance, such as, for example HRP, a fluorescent label, a radioisotope, beta-galactosidase, and alkaline phosphatase. In another embodiment, the detectable substance is immobilized on a solid support (e.g., a microtiter plate).

In certain embodiments, the capture antibody and the revelation antibody are anti-sPLA2-IIA monoclonal antibodies, particularly the anti-sPLA2-IIA monoclonal antibodies designated 6G2 and 9C8. In one kit of the invention for practicing the sandwich ELISA method, the capture antibody is anti-sPLA2-IIA monoclonal antibody 6G2, optionally immobilized on a microtiter plate, and the revelation antibody is HRP-labeled 9C8. Chemicals for detecting and quantitating the level of revelation antibody bound to the solid support (which directly correlates with the level of sPLA2-IIA in the sample) may be optionally included in the kit. Purified sPLA2-IIA may also be provided as an antigen standard.

In another embodiment, the antibodies of the present invention may be used in vivo to identify tissues and organs or cells that express sPLA2-IIA.

The method comprises the steps of administering a detectably labeled anti-sPLA2-IIA antibody or a pharmaceutical composition thereof to a patient in need of such a diagnostic test and subjecting the patient to imaging analysis to determine the location of the antibody or fragment bound-sPLA2-IIA-expressing tissues. Imaging analysis is well known in the medical art, and includes, without limitation, X-ray analysis, magnetic resonance imaging (MRI) or computed tomography (CT). In another embodiment of the method, a biopsy is obtained from the patient to determine whether a tissue of interest expresses sPLA2-IIA rather than subjecting the patient to imaging analysis. As stated above, in an embodiment of the invention, the anti-sPLA2-IIA antibodies are labeled with a detectable agent that can be imaged in a patient. For example, the antibody may be labeled with a contrast agent, such as barium, which can be used for X-ray analysis, or a magnetic contrast agent, such as a gadolinium chelate, which can be used for MRI or CT. Other labeling agents include, without limitation, radioisotopes, such as (99)Tc; or other labels discussed herein. These methods may be used, e.g., to diagnose sPLA2-IIA-mediated disorders or track the progress of treatment for such disorders.

EXAMPLES

Figure 1:
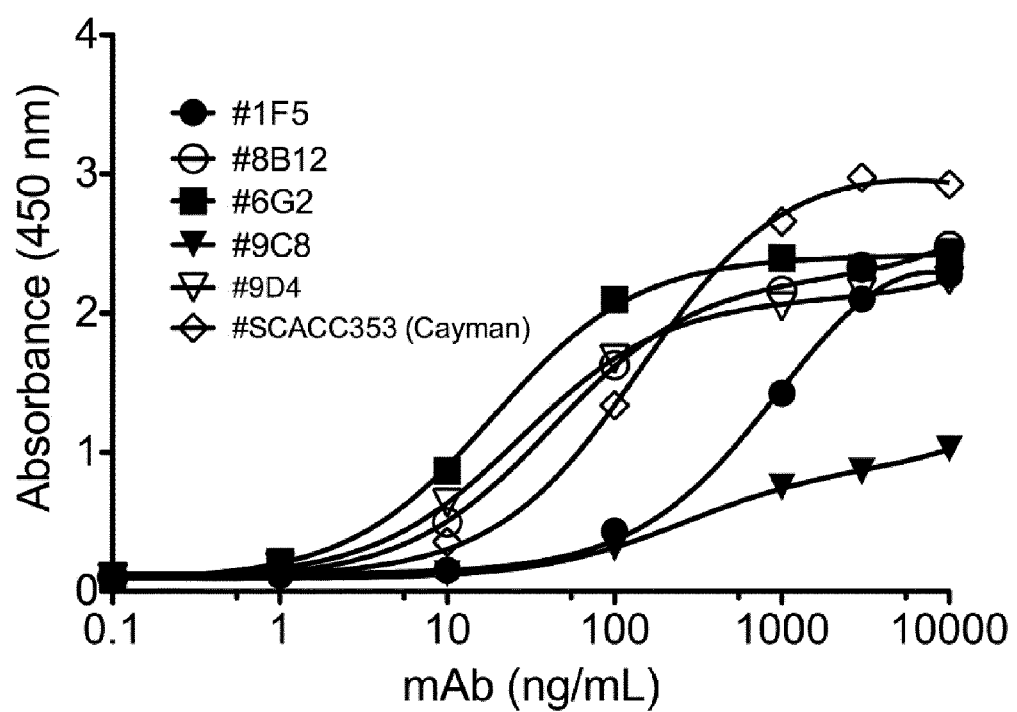
FIG. 1: Dilution curves of sPLA2-IIA antibodies in indirect ELISA

The present invention is further illustrated by the following examples.

Example 1

Production of Human Recombinant sPLA2-IIA Protein

Human sPLA2-IIA (N1A mutant) was produced according to published procedures (Othman et al. Biochim Biophys Acta 1996, 1303:92-102; Bezzine et al. J. Biol. Chem. 2000, 275: 3179-3191; Singer et al J Biol Chem 2002, 277: 48535-48549) with modifications as described below.

The general outline of the recombinant production of human $sPLA_2$-IIA performed in $E\ coli$ is as follows:
1. Subcloning of human $sPLA_2$ cDNA (N1A variant) into the pET21a expression vector
2. Transformation of $E.\ coli$ BL21 and protein expression in large scale
3. Inclusion body preparation
4. Reduction and sulfonation
5. Solubilization in a high chaotrope buffer
6. Refolding by rapid dilution in a low chaotrope buffer
7. Concentration and purification by reverse phase HPLC
8. Lyophilisation, protein quantification and structural/functional analysis ($OD_{280nm}$, MALDI-TOF, SDS-PAGE gel, enzymatic activity)

1. Subcloning of Human $sPLA_2$-IIA cDNA into the pET21 a Vector

The cDNA coding for the human mature enzyme was PCR-amplified and cloned in frame to the initiator Met codon encoded by the NdeI site present in the pET21a expression plasmid (Novagen Inc.). This vector thus allows the production of the $sPLA_2$ as a non fusion protein, i.e. without any additional amino acid. This strategy likely improves the yield of the refolding step and also avoids a cleavage step with proteases like factor $X_a$ or trypsin, which usually decreases the overall yield.

2. Transformation of E. coli BL21 Rosetta or BL21-CodonPlus (DE3) and Protein Expression Protein expression was performed after transformation of the human sPLA2-IIA-pET21a construction into chemically competent E. coli Rosetta BL21 DE3 pLYS (Novagen) or BL21 DE3 CodonPlus (Stratagene) and selection of colonies on Luria Broth/agar/ampicillin (100 µg/ml)/Chloramphenicol (34 µg/ml) plates. A single ampicillin-resistant colony was grown in 10 ml of Terrific Broth medium with ampicillin (100 µg/ml) (TB/A) and incubated under agitation at 37° C. for about 4 h. The preculture is then diluted to 2 liters of TB/A and further grown to ~1.0 $OD_{600nm}$. IPTG (0.5 mM) is then added to induce protein expression for overnight at 37° C. The next day, the bacteria are pelleted, lyzed and the inclusion bodies are purified.

3. Inclusion Body Preparation

Lysis buffer with and without detergent were prepared as described in Table 1.

TABLE 1

Lysis buffer with detergent. For Lysis buffer without detergent, Triton X-100 and DOC are omitted.

| Component | Final concentration |
| --- | --- |
| Tris pH 8.0 | 50 mM |
| NaCl | 50 mM |
| EDTA | 2 mM |
| PMSF | 1 mM |
| Triton X-100 | 1% |
| $Na^+$-Deoxycholate (DOC) | 1% |

Overnight cultures of IPTG-induced bacteria (2 liters) were harvested and spun down for 30 min at 4° C. and 5,000 rpm. The bacterial pellet was then resuspended in 100 ml of lysis buffer with detergent. Lysis was performed after adding 5 mg lysozyme, 1.5 mg DNAse I and 10 mM $MgCl_2$, and extensive sonication followed by incubation for 1 h at 37° C. in a water bath with gentle agitation. In some cases, bacterial lysis was performed after resuspension in lysis buffer without detergent (containing lysozyme, DNAse I and $MgCl_2$) and homogeneization with a French press apparatus (1200 pSi, two passages). After lysis, the solution was spun down for 15 min at 4° C. and 10,000 rpm. The protein pellet was then washed extensively, once in lysis buffer with detergent, and at least twice in lysis buffer without detergent. For each washing, the pellet was resuspended in lysis buffer using a dounce homogenizer, and then centrifugated for 15 min at 4° C. and 10,000 rpm. After the last centrifugation, the supernatant is discarded and pellets containing purified sPLA2 protein inclusion body are stored at −20° C. These pellets were analyzed for the presence of the expected mature sPLA2 protein and purity by SDS-PAGE analysis and MALDI-TOF mass spectrometry after solubilization and reduction in a chaotropic buffer (50 mM Tris pH 8.0, 8 M Urea or 7 M guanidine, 10 mM DTT). At this step, the overall yield is usually around 50 to 100 mg of unfolded sPLA2 protein/liter of cell culture.

4. Reduction and Sulfonation of Inclusion Body

Inclusion body pellet containing human sPLA2-IIA (up to 100 mg) was solubilized in 40 ml of 7 M guanidine, 50 mM Tris pH 8.0, 0.3 $MNa^+$ Sulfite. After 1 h, 10 to 20 ml of NTSB reagent (ratio NTSB/cysteine in sPLA2>5) was added and incubated up to overnight at 25° C. depending on the protein solubility (in some cases, urea was used instead of guanidine). The reaction is over when the colour of the solution turned slightly yellow (the solution is initially red orange). After solubilization and reduction, the protein solution was spun down to remove insoluble aggregates, and the supernatant was dialyzed (membrane tubing with a cut-off of 8 kDa) against 4 l of 0.1% acetic acid with 3 buffer exchanges every 2 h. The sulfonated and precipitated sPLA2-IIA protein (white powder) was recovered and spun down to obtain a dried pellet which was stored at −20° C. before refolding.

5. Refolding Procedure, HPLC Purification and Structural/Functional Analyses

Human sPLA2-IIA mutant N1A was refolded according to published procedures (Othman, et al, Biochim. Biophys. Acta, 1996, 1303, 92-102 and Koduri, et al, J. Biol. Chem. 2002 277, 5849-5857). Briefly, the sulfonated N1A human sPLA2-IIA protein was dissolved in 6 M Guanidine, 50 mM Tris/HCl pH 8.0 at 1 mg/ml and refolded by dialysis at 4° C. for 48 h against a refolding buffer consisting of 25 mM Tris/HCl pH 8.0, 5 mM $CaCl_2$, 5 mM L-Cysteine and 0.9 M Guanidine/HCl). The protein was further dialyzed against 20 mM Tris/HCl pH 7.4 and the protein solution was centrifuged. The precipitated protein was dissolved in 30% ACN, 0.1% TFA and clarified by centrifugation. The soluble protein was filtered, quantified for protein amount by $OD_{280nm}$ and loaded into several runs onto a C18 semi-preparative reverse phase HPLC column (250×10 mm, 5 µm, 100 Å, $C_2$ endcapping, Macherey-Nagel) pre-equilibrated with 20% solvent B in solvent A (Solvent A: $H_2O$/0.1% TFA/1 mM L-Methionine; solvent B: ACN/0.1% TFA/1 mM L-Methionine). After injection, a solvent gradient was started: 20% B to 45% B in 75 min, then to 95% B in 20 min (flow rate 3 ml/min). HPLC fractions were checked for sPLA2 enzymatic activity and molecular mass by MALDI-TOF mass spectrometry. Mature properly folded (i.e. active) non oxidized human sPLA2-IIA eluted at the beginning of the major peak containing sPLA2 activity. The active fractions containing the human sPLA2-IIA protein were combined, lyophilized, re-suspended in 20% ACN/0.1% TFA and loaded onto a C18 symmetry shield analytical column using solvents A and B without L-Methionine and a linear gradient of ACN in water from 20% to 40% ACN in 100 min (flow rate 1 ml/min). Fractions were collected manually according to $OD_{280nm}$. The active properly folded fractions (identified as above) were combined, lyophilized, re-suspended in 30% ACN/0.1% TFA, and analyzed for protein amount ($OD_{280nm}$ and SDS-PAGE) and quality (MALDI-TOF mass spectrometry and specific enzymatic activity). The overall yield of pure, refolded human sPLA2-IIA is about 1-2 mg/liter of bacterial culture. The protein was judged to be >98% pure on a 15% SDS-polyacrylamide gel. The observed molecular mass (MALDI-TOF mass spectrometry, mass measured in linear mode using sinapinic acid as a matrix, Applied Biosystems TOF-TOF 4800 apparatus) is less than 1 Da different from the calculated mass (13, 860.86 Da). The specific enzymatic activity was measured using radiolabeled autoclaved E. coli membranes as phospholipid substrate (Rouault, M., Le Calvez, C., Boilard, E., Surrel, F., Singer, A., Ghomashchi, F., Bezzine, S., Scarzello, S., Bollinger, J., Gelb, M. H., and Lambeau, G. (2007) Recombinant production and properties of binding of the full set of mouse secreted phospholipases A2 to the mouse M-type receptor, Biochemistry 46, 1647-1662). The recombinant protein was aliquoted, lyophilized and stored at 20° C.

Example 2

Generation of Anti-sPLA2-IIA Antibodies and Direct Comparison of Antibodies by Indirect ELISA Five different monoclonal anti-sPLA2-IIA antibodies (#1F5, #6G2, #8B12, #9C8 and #9D4 clones) were produced by immunizing mice with recombinant human sPLA2-IIA N1A produced as in Example 1. mAb were purified by protein A affinity and quantified.

Direct comparison of different mAbs was performed by indirect ELISA.

Microplate wells were coated with 50 ng of recombinant human sPLA2-IIA N1A in PBS pH 7.5, overnight at room temperature. Sample wells were washed three times with PBS containing 0.05% Tween 20. After final washing, sample wells were treated with blocking solution containing 1% bovine serum albumin (BSA) in PBS buffer for 60 min at room temperature. Following washing with PBS containing 0.05% Tween 20, increasing amounts (0.1 ng/mL up to 10 µg/mL) of mAb directed against human sPLA2-IIA N1A were added to antigen-coated wells, and incubated for 120 min at room temperature. Following washing with PBS containing 0.05% Tween 20, the binding of mAb was detected by treatment with HRP-conjugated polyclonal goat anti-mouse IgG (Abcam ab7068) for 60 min at room temperature. TMB was added, reaction was stopped and absorbance at 450 nm was determined on an Optima FluoStar microplate reader (BMG Labtech).

The resulting dilution curves are depicted in FIG. 1.

Data were fitted with a one-site saturation model and the relative Kd values were estimated from the model (Table 2 below). MW Antibodies were 150 kDa for IgG, at 975 kDa for IgM and at 195 kDa for IgM-IgGlike.

Microplate wells were coated with 50 ng of recombinant human sPLA2-IIA N1A in PBS pH 7.5, overnight at room temperature. Sample wells were washed three times with PBS containing 0.05% Tween 20. After final washing, sample wells were treated with blocking solution containing 1% bovine serum albumin (BSA) in PBS buffer for 60 min at room temperature.

Following washing with PBS containing 0.05% Tween 20, increasing amounts (1 ng/mL up to 1 µg/mL) of mAb and biotinylated-mAb directed against human sPLA2-IIA were added to antigen-coated wells, and incubated for 60 min at room temperature. Following washing with PBS containing 0.05% Tween 20, the binding of mAb was detected by treatment with HRP-conjugated polyclonal goat anti-mouse IgG (Abcam ab7068) or High Sensitivity Streptavidin-HRP (Thermo fisher 21130) for 60 min at room temperature. TMB was added, reaction was stopped and absorbance at 450 nm was determined on an Optima FluoroStar microplate reader (BMG Labtech).

Figure 2:
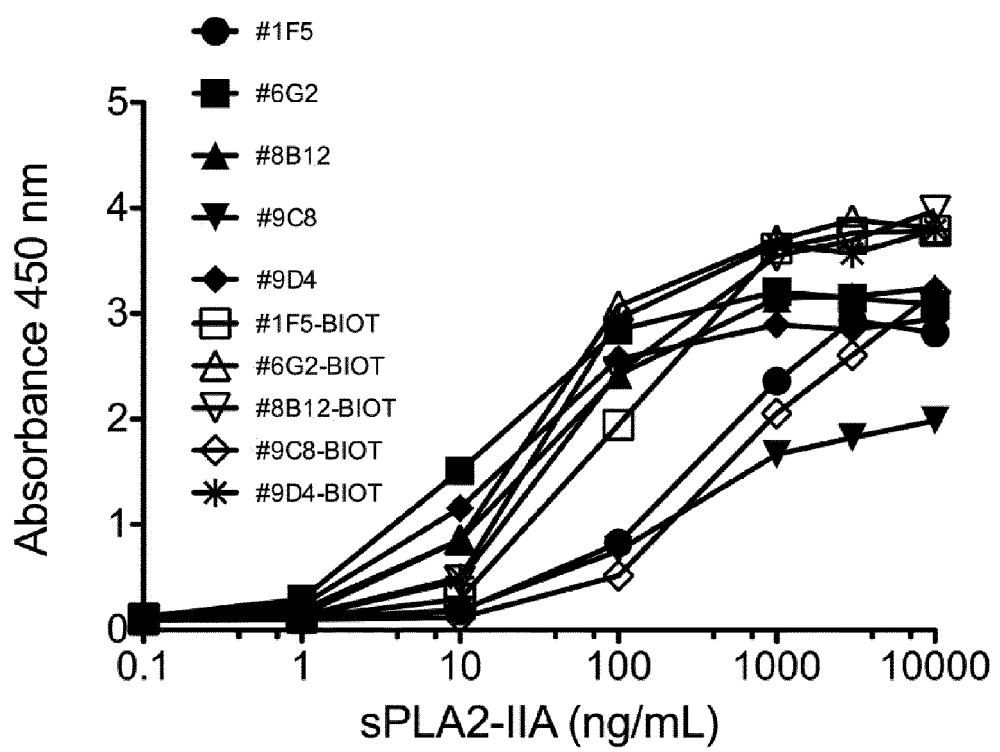
FIG. 2: Affinity comparison between biotinylated antibodies and non-biotinylated antibodies.

Data were fitted with a one-site saturation model and Kd values were estimated from the model (Table 3 below). As depicted in FIG. 2 and in Table 3, the results showed that biotinylation of the different mAbs did not significantly

TABLE 2

| | #1F5 (IgM) | #1F5 (IgG-like) | #6G2 | #8B12 | #9C8 | #9D4 | SCACC353 (Cayman) |
|---|---|---|---|---|---|---|---|
| Kd (M) | $1.059 \times 10^{-9}$ | $5.296 \times 10^{-9}$ | $1,240 \times 10^{-10}$ | $2.804 \times 10^{-10}$ | $1.712 \times 10^{-9}$ | $1.816 \times 10^{-10}$ | $9.479 \times 10^{-10}$ |
| $R^2$ | 0.9990 | 0.9990 | 0.9988 | 0.9997 | 0.9997 | 0.9998 | 0.9993 |

As indicated in the table above, these results clearly showed that the three mAbs #6G2, #8B12 and #9D4 display much higher affinity than the commercially available monoclonal antibody (ref. SCACC353, Cayman Chemicals) towards recombinant human sPLA2-IIA.

affect the affinity profiles to recombinant human sPLA2-IIA. Revelation with Streptavidin-HRP led to amplification of the signal.

TABLE 3

| | | #1F5 | | #6G2 | #8B12 | #9C8 | #9D4 |
|---|---|---|---|---|---|---|---|
| One site model | | IgM | IgG like | IgG1 | IgG1 | IgG1 | IgG1 |
| Purified Antibodies | Kd (mol/L) | $3.971 \times 10^{-10}$ | $1.986 \times 10^{-9}$ | $8.171 \times 10^{-11}$ | $2,159 \times 10^{-10}$ | $1,167 \times 10^{-9}$ | $1.071 \times 10^{-10}$ |
| | R square | 0.9991 | 0.9991 | 0.9997 | 0.9998 | 0.9999 | 0.9994 |
| Biotinylated Antibodies | Kd (mol/L) | $1.148 \times 10^{-10}$ | $5.738 \times 10^{-10}$ | $2.198 \times 10^{-10}$ | $3.873 \times 10^{-10}$ | $3.336 \times 10^{-9}$ | $2.642 \times 10^{-10}$ |
| | R square | 0.9993 | 0.9993 | 0.9985 | 0.9989 | 0.9996 | 0.9922 |

Example 3

Biotinylation of Anti-sPLA2-IIA Antibodies and Development of Sandwich ELISA 1 mg of each monoclonal antibody antibodies #1F5, #6G2, #8B12, #9C8 and #9D4 were biotinylated by using a Pierce kit (ref.21435). Labeled antibodies were stored at −20° C.

Specific immunoreactivity to recombinant human sPLA2-IIA was compared using biotinylated mAbs #1F5, #6G2, #8B12, #9C8 and #9D4) to non-biotinylated mAbs using an indirect ELISA.

A human sPLA2-IIA sandwich ELISA was constructed by using the reagents described above. The different single pairs of non-labeled coating antibodies (5 µg/mL) and revelation with biotinylated-antibodies (ranging from 10 ng/mL to 3 µg/mL) were tested. The positive signal was determined on a sPLA2-IIA range (from 0 and 1 ng/mL to 100 ng/mL).

Different parameters such as nature of microplate, final volume in the well, time and temperature of incubation, nature and concentrations of streptavidin-HRP, composition of assay buffer, nature and concentration of added detergents, were studied to optimize the assay. Mixtures of Revelation Antibodies or mixes of Coating Antibodies were not retained. Mixtures didn't show a synergy effect, on the contrary, background was added when the positive signal was limited to the best single pair signal. The positive signal with mixes pair was similar to the single pair signal.

The #9C8 mAb appeared to be the most efficient coating antibody to capture sPLA2-IIA in conditions where the revelation is performed with #6G2-Biot.

In conclusion, the following pair was retained: #9C8 at 3 μg/mL and #6G2-Biot at 1 μg/mL.

Typical assay conditions were thus as follows: 96-wells microplate (High Binding Greiner ref. 655061) were incubated overnight in Carbonate Buffer 100 mM pH 9.6 at room temperature with 50 μL of #9C8 at 3 μg/mL. Afterwards wells were aspirated and washed 3 times with 300 μL of PBS containing 0.05% Tween 20. After final washing, sample wells were treated with blocking solution containing 1% bovine serum albumin (BSA) in PBS buffer for 60 min at 37° C. Following washing with PBS containing 0.05% Tween 20, recombinant human sPLA2-IIA standards (varying concentrations of protein in assay buffer consisting of PBS 1×, BSA 0.5%, Tween20 0.05%) were added to the wells to generate a calibration curve. Serum or plasma samples were diluted 10-fold in PBS 1×, BSA 0.5%, and added to their respective wells and the ELISA plate was incubated for 2 h at 37° C. After aspiration, wells were washed 3 times with PBS containing Tween 20 0.05%, and 50 μL/well of the #6G2-Biot at 1 μg/mL was added to the wells for 1 h at 37° C. Following washing with PBS containing 0.05% Tween 20, the binding of #6G2-Biot mAb was revealed by incubation with 25 ng/mL of Strepta-Poly HRP (Thermofisher ref. 21140) for 30 min at 37° C. TMB substrate was added, reaction was stopped and absorbance at 450 nm was determined on an Optima FluoroStar microplate reader (BMG Labtech).

Example 4

Evaluation of Assay Performances

Assay Specificity

Figure 3:
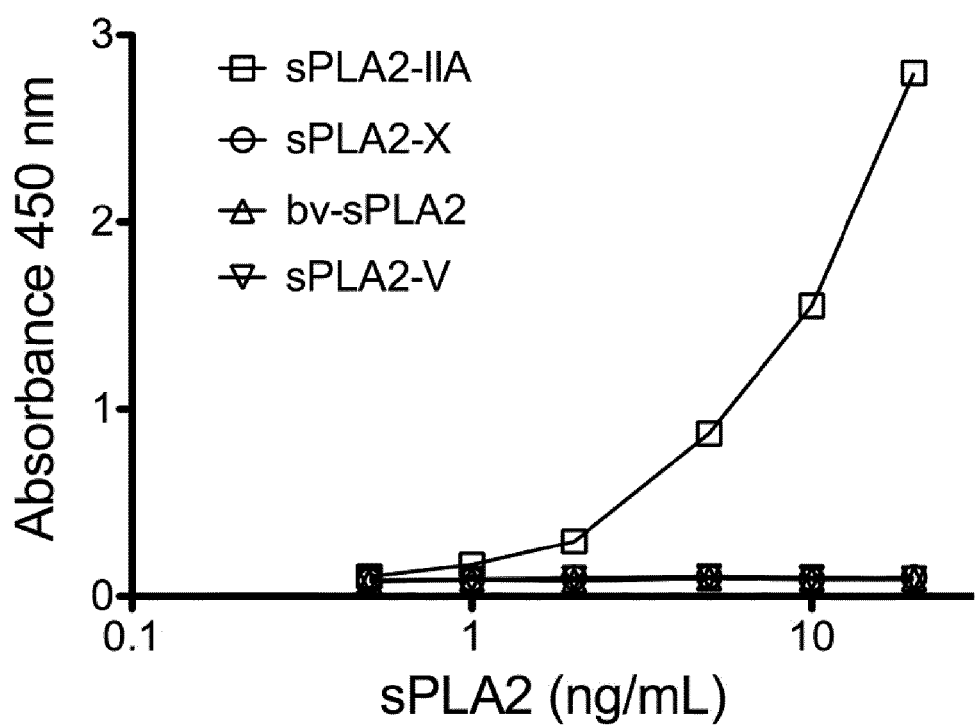
FIG. 3: Sandwich ELISA test with 9C8 and 6G2-biot antibodies.

To assess the specificity of the ELISA test for recombinant human sPLA2-IIA, recombinant human sPLA2-IIA, sPLA2-IID, sPLA2-V and sPLA2-X; recombinant mouse sPLA2-IB, sPLA2-IIA, sPLA2-IID, sPLA2-IIF, sPLA2-V and sPLA2-X; and purified bee venom sPLA2 (bvPLA2) were tested at concentrations up to 1000 ng/mL. Recombinant proteins were obtained as described in Singer et al, 2002 and Rouault et al, 2007. The ELISA test displayed very high specificity and did not recognize human sPLA2-X, human sPLA2-V and bvsPLA2 (FIG. 3) nor recombinant mouse sPLA2-IB, sPLA2-IIA, sPLA2-IID, sPLA2-IIF, sPLA2-V and sPLA2-IIA (data not shown).

Assay Sensitivity

Figure 4:
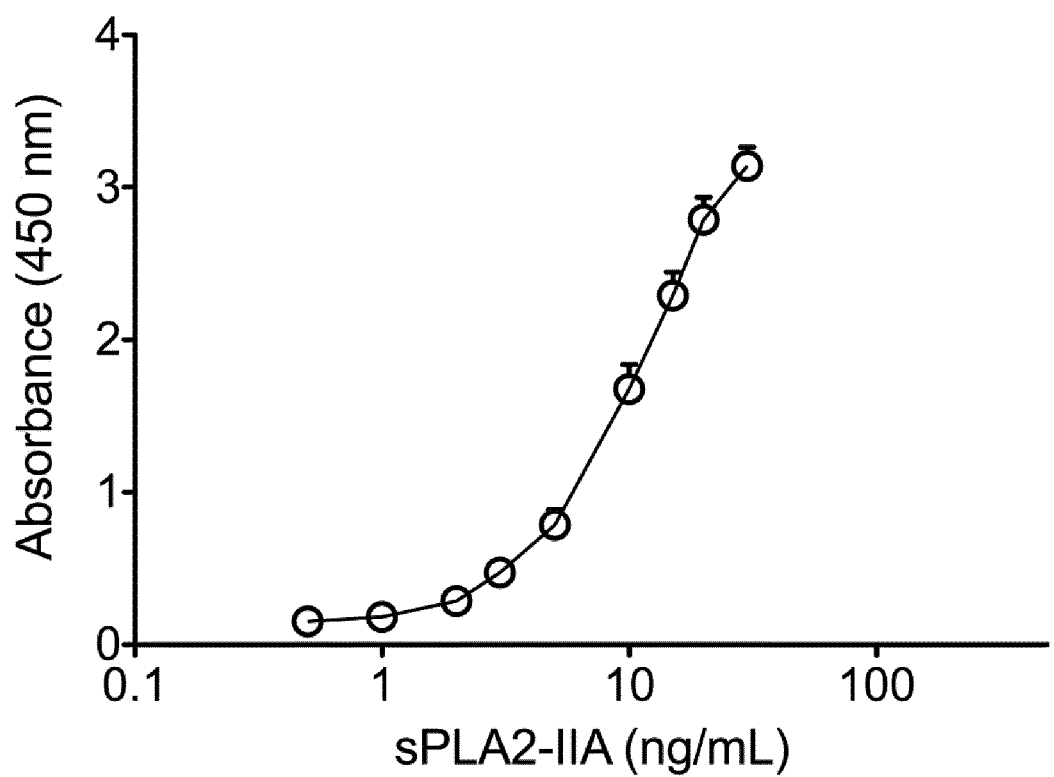
FIG. 4: Typical calibration curve and 3-SD evaluation obtained from the sandwich ELISA test.

FIG. 4 shows a typical calibration curve obtained with the final ELISA orientation described above, in which human sPLA2-IIA protein was prepared at a concentration of 10 μM and serially diluted to create a calibration curve.

Based on a mean+SD evaluation from the zero calibrator, the limit of quantification of the ELISA was determined to be 0.5 ng/mL.

Assay Variation

The intra-assay coefficient of variation (CV) was assessed by calculating the average CV from four standard calibration curves ranging from 0 to 30 ng/mL in duplicate or eight standard calibration curves ranging from 0 to 100 ng/mL in quadruplicate and with two operators. The inter-assay CV was determined by calculating the mean optical density per concentration and associated Standard deviation (SD) and by calculating the mean CV as for intra-assay CV. When considering data from several assays, intra and inter-assay CV were 4.5%±0.019 and 18%±0.127, respectively.

Assay Recovery

To assess the recovery of human sPLA2-IIA present in human serum, human recombinant sPLA2-IIA protein was spiked at concentrations of 1, 2 and 3 ng/mL to a human EDTA plasma sample containing endogenous sPLA2-IIA at a mean (SD) concentration of 4.7 (0.1) ng/mL. This samples was then analyzed by using the sandwich ELISA and mean (SD) results were 5.7 (0.8) ng/mL, 6.7 (0.7) ng/mL, and 7.8 (0.8) ng/mL, resulting in a 100%, 98% and 97% recovery, respectively.

Example 5

Determination of sPLA2-IIA Concentration in Human Plasma Samples

The ELISA sandwich described above was used to assay human plasma samples from chest pain at emergency (n=318). sPLA2 enzymatic activity was also measured in these samples using a selective fluorimetric method (AteroDX® Activity, Aterovax, Paris, France). Results are expressed in Unit per mL of sample (U/mL), with one unit defined as the amount of sPLA2 enzyme which catalyses the release of one nmole of product per min. The detection limit of the assay is 17 U/mL with an upper linear analytical range of 232 U/mL and a functional sensitivity (20%) of 21 U/mL. Average within-run variability and average intra-assay variability are 5.9% and 8.9%, respectively. sPLA2-IIA mass ranged from 0.5 to 32.7 ng/mL in these samples with a mean (SD) of 3.2 (5.2) ng/mL.

Figure 5:
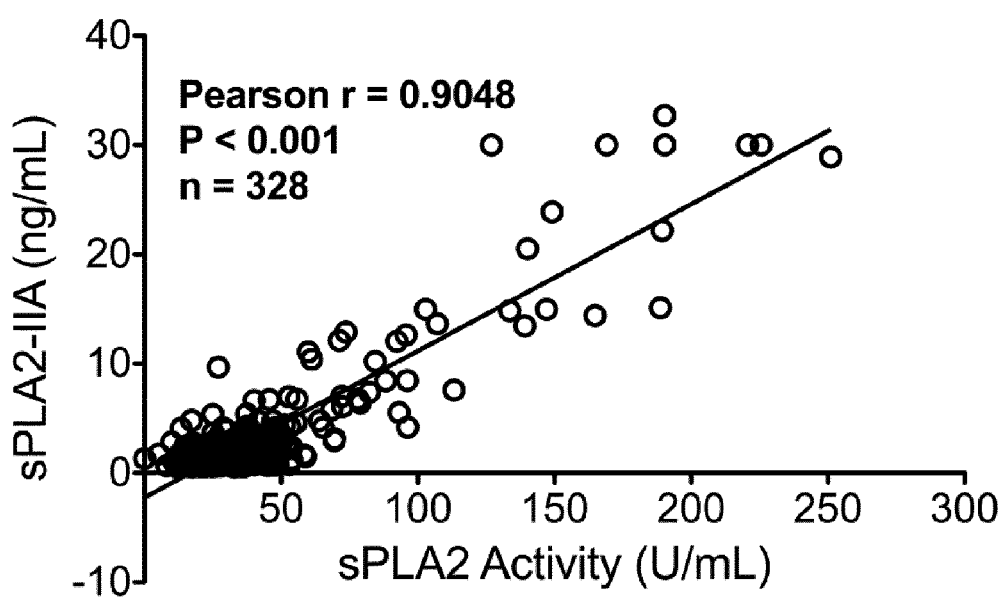
FIG. 5: Correlation between sPLA2-IIA mass and sPLA2 enzymatic activity in chest pain patients.

As illustrated in FIG. 5, correlation between sPLA2-IIA mass and sPLA2 activity values was high in these samples.

The invention claimed is:

1. An isolated antibody comprising a variable region of a heavy chain and a variable region of a light chain, wherein:
the variable region of the heavy chain comprises the following CDRs: GYTFTS (SEQ ID NO: 1), WIFPGDGSTE (SEQ ID NO: 2) and WGITAFPLFDY (SEQ ID NO: 3);
the variable region of the light chain comprises the following CDRs: RASESVDYDGDSYMN (SEQ ID NO: 4), AASNLES (SEQ ID NO: 5) and LQSNEAPWT (SEQ ID NO: 6); and
wherein said antibody has a dissociation constant ($K_d$) for binding to human secretory phospholipase A2 IIA (sPLA2-IIA) less than $9 \times 10^{-10}$ M.

2. The isolated antibody according to claim 1, wherein:
the amino acid sequence encoding the heavy chain variable region is SEQ ID NO: 13 and
the amino acid sequence encoding the light variable region is SEQ ID NO: 14.

3. The antibody of claim 1, wherein the antibody is a chimeric antibody.

4. The antibody of claim 1, wherein the antibody is labeled with a detectable label.

5. The antibody of claim 1, wherein the antibody is humanized.

6. A composition comprising an antibody according to claim 1.

7. A kit comprising at least one antibody according to claim 1.

8. The kit according to claim 7, comprising:
a first antibody comprising:
a variable region of the heavy chain comprising the following CDRs: GYTFTS (SEQ ID NO: 1), WIFPGDGSTE (SEQ ID NO: 2) and WGITAFPLFDY (SEQ ID NO: 3); and
a variable region of the light chain comprising the following CDRs: RASESVDYDGDSYMN (SEQ ID NO: 4), AASNLES (SEQ ID NO: 5) and LQSNEAPWT (SEQ ID NO: 6); and
a second antibody comprising:
a variable region of the heavy chain comprising the following CDRs: GFTFSS (SEQ ID NO: 7), AINSNGGSTY (SEQ ID NO: 8) and QGYGNFFDY (SEQ ID NO: 9); and
a variable region of the light chain comprising the following CDRs: RSSQSIVHSNGNTYLY (SEQ ID NO: 10), RVSNRFS (SEQ ID NO: 11) and FQGTHVPRT (SEQ ID NO: 12).

9. A method for detecting sPLA2-IIA in a biological sample, comprising:
contacting said biological sample with an antibody according to claim 1 and
detecting the anti-sPLA2-IIA antibody bound to sPLA2-IIA, thereby indicating the presence of sPLA2-IIA in said biological sample.

10. The method according to claim 9, further defined as a method of performing an in vitro diagnostic or prognostic assay for determining the presence of sPLA2-IIA in a biological sample using the antibody.

11. The method according to claim 10, wherein the assay is a sandwich ELISA using a coating antibody and a revealing antibody, wherein the coating antibody comprises:

a variable region of the heavy chain comprising the following CDRs: GYTFTS (SEQ ID NO: 1), WIFPGDGSTE (SEQ ID NO: 2) and WGITAFPLFDY (SEQ ID NO: 3); and a variable region of the light chain comprising the following CDRs: RASESVDYDGDSYMN (SEQ ID NO: 4), AASNLES (SEQ ID NO: 5) and LQSNEAPWT (SEQ ID NO: 6).

12. The method according to claim 11, wherein:

the variable region of the heavy chain of the revealing antibody comprises the following CDRs: GFTFSS (SEQ ID NO: 7), AINSNGGSTY (SEQ ID NO: 8) and QGYGNFFDY (SEQ ID NO: 9); and the variable region of the light chain of the revealing antibody comprises the following CDRs: RSSQSIVHSNGNTYLY (SEQ ID NO: 10), RVSNRFS (SEQ ID NO: 11) and FQGTHVPRT (SEQ ID NO: 12).

13. The method according to claim 11, wherein:

the amino acid sequence encoding the heavy chain variable region of the revealing antibody is SEQ ID NO: 15; and the amino acid sequence encoding the light chain variable region of the revealing antibody is SEQ ID NO: 16.

14. An expression vector comprising at least one of SEQ ID NO: 17, SEQ ID NO: 18, SEQ ID NO: 19, and SEQ ID NO: 20.

15. A hybridoma cell line producing an antibody against human secretory phospholipase A2 IIA (sPLA2-IIA) registered under CNCM 1-4587 or CNCM 1-4588.

* * * * *

UNITED STATES PATENT AND TRADEMARK OFFICE
CERTIFICATE OF CORRECTION

PATENT NO. : 9,637,553 B2  
APPLICATION NO. : 14/387430  
DATED : May 2, 2017  
INVENTOR(S) : Gerard Lambeau, Emmanuel Valentin and Melanie Rennou Page 1 of 1

It is certified that error appears in the above-identified patent and that said Letters Patent is hereby corrected as shown below:

On the Title Page

Item (30) Foreign Application Priority Data:
Delete "12161036" and replace with -- 12161036.4 --.

Signed and Sealed this
Twenty-third Day of July, 2019

Andrei Iancu
*Director of the United States Patent and Trademark Office*

SEQUENCE LISTING

<160> NUMBER OF SEQ ID NOS: 22

<210> SEQ ID NO 1
<211> LENGTH: 6
<212> TYPE: PRT
<213> ORGANISM: Artificial Sequence
<220> FEATURE:
<223> OTHER INFORMATION: VH-CDR1

<400> SEQUENCE: 1

Gly Tyr Thr Phe Thr Ser
1               5

<210> SEQ ID NO 2
<211> LENGTH: 10
<212> TYPE: PRT
<213> ORGANISM: Artificial Sequence
<220> FEATURE:
<223> OTHER INFORMATION: VH-CDR2

<400> SEQUENCE: 2

Trp Ile Phe Pro Gly Asp Gly Ser Thr Glu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: VH-CDR3

<400> SEQUENCE: 3

Trp Gly Ile Thr Ala Phe Pro Leu Phe Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: VL-CDR1

<400> SEQUENCE: 4

Arg Ala Ser Glu Ser Val Asp Tyr Asp Gly Asp Ser Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: VL-CDR2

<400> SEQUENCE: 5

Ala Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL-CDR3

<400> SEQUENCE: 6

Leu Gln Ser Asn Glu Ala Pro Trp Thr
1               5

<210> SEQ ID NO 7
<211> LENGTH: 6
<212> TYPE: PRT
<213> ORGANISM: Artificial Sequence
<220> FEATURE:
<223> OTHER INFORMATION: VH-CDR1

<400> SEQUENCE: 7

Gly Phe Thr Phe Ser Ser
1               5

-continued

```
<210> SEQ ID NO 8
<211> LENGTH: 10
<212> TYPE: PRT
<213> ORGANISM: Artificial Sequence
<220> FEATURE:
<223> OTHER INFORMATION: VH-CDR2

<400> SEQUENCE: 8

Ala Ile Asn Ser Asn Gly Gly Ser Thr Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: VH-CDR3

<400> SEQUENCE: 9

Gln Gly Tyr Gly Asn Phe Phe Asp Tyr
1               5

<210> SEQ ID NO 10
<211> LENGTH: 16
<212> TYPE: PRT
<213> ORGANISM: Artificial Sequence
<220> FEATURE:
<223> OTHER INFORMATION: VL-CDR1

<400> SEQUENCE: 10

Arg Ser Ser Gln Ser Ile Val His Ser Asn Gly Asn Thr Tyr Leu Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: VL-CDR2

<400> SEQUENCE: 11

Arg Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: VL-CDR3

<400> SEQUENCE: 12

Phe Gln Gly Thr His Val Pro Arg Thr
1               5

<210> SEQ ID NO 13
<211> LENGTH: 120
<212> TYPE: PRT
<213> ORGANISM: Artificial Sequence
<220> FEATURE:
<223> OTHER INFORMATION: Heavy Chain Variable Region

<400> SEQUENCE: 13

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30
```

```
Asp Ile Asn Trp Val Arg Gln Arg Pro Glu Gln Gly Leu Glu Trp Ile
            35                  40                  45

Gly Trp Ile Phe Pro Gly Asp Gly Ser Thr Glu Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Gly Ile Thr Ala Phe Pro Leu Phe Asp Tyr Trp Gly Gln
            100                 105                 110

Gly Thr Ala Leu Thr Val Ser Ser
            115                 120

<210> SEQ ID NO 14
<211> LENGTH: 112
<212> TYPE: PRT
<213> ORGANISM: Artificial Sequence
<220> FEATURE:
<223> OTHER INFORMATION: Light Chain Variable Region

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Ser Asn
                85                  90                  95

Glu Ala Pro Trp Thr Phe Gly Gly Gly Thr Lys Leu Glu Ile Lys Arg
            100                 105                 110

<210> SEQ ID NO 15
<211> LENGTH: 118
<212> TYPE: PRT
<213> ORGANISM: Artificial Sequence
<220> FEATURE:
<223> OTHER INFORMATION: Heavy Chain Variable Region

<400> SEQUENCE: 15

Asp Val Glu Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Gln Gly Tyr Gly Asn Phe Phe Asp Tyr Trp Gly Gln Gly Thr
```

```
                  100                 105                 110

Thr Leu Thr Val Ser Ser
            115

<210> SEQ ID NO 16
<211> LENGTH: 113
<212> TYPE: PRT
<213> ORGANISM: Artificial Sequence
<220> FEATURE:
<223> OTHER INFORMATION: Light Chain Variable Region

<400> SEQUENCE: 16

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Phe Gln Gly
                85                  90                  95

Thr His Val Pro Arg Thr Phe Gly Gly Gly Thr Asn Leu Glu Ile Lys
            100                 105                 110

Arg

<210> SEQ ID NO 17
<211> LENGTH: 360
<212> TYPE: DNA
<213> ORGANISM: Artificial Sequence
<220> FEATURE:
<223> OTHER INFORMATION: Heavy Chain Variable Region

<400> SEQUENCE: 17
caggttcagc tgcagcagtc tggagctgaa ctggtaaagc ctggggcttc agtgaagttg      60
tcctgcaagg cttctggcta caccttcaca agctatgata taaactgggt gaggcagagg     120
cctgaacagg gacttgagtg gattggatgg attttttcctg agatggtag tactgagtac      180 aatgagaagt tcaagggcaa ggccacactg actacagaca atcctccag cacagcctac      240 atgcagctca gcaggctgac atctgaggac tctgctgtct atttctgtgc aaggtggggt      300
attacggctt tccccctttt tgactactgg ggccaaggca ccgctctcac agtctcctca     360

<210> SEQ ID NO 18
<211> LENGTH: 336
<212> TYPE: DNA
<213> ORGANISM: Artificial Sequence
<220> FEATURE:
<223> OTHER INFORMATION: Light Chain Variable Region

<400> SEQUENCE: 18
gacattgtgc tgacccaatc tccagcttct ttggctgtgt ctctagggca gagggccacc      60
atctcctgca gagccagcga agtgttgat tatgatggcg atagttatat gaactggtac     120
caacagaaac caggacagcc accgaaactc ctcatctatg ctgcatccaa tctagaatct     180 gggatcctg ccaggtttag tggcagtggg tctgggacag acttcaccct caacattcat     240
cctgtggagg aggaggatgc tgcaacctat tactgtctgc aaagtaatga ggctccgtgg     300
```

```
acgttcggtg gaggcaccaa gctggaaatc aaacgg                              336
```

<210> SEQ ID NO 19
<211> LENGTH: 354
<212> TYPE: DNA
<213> ORGANISM: Artificial Sequence
<220> FEATURE:
<223> OTHER INFORMATION: Heavy Chain Variable Region

<400> SEQUENCE: 19

```
gacgtggagc tcgtggagtc tgggggaggc ttagtgaagc ttggagggtc cctaaaactc    60
tcctgtgcag cctctggatt cactttcagt agctattaca tgtcttgggt tcgccagact   120
ccagagaaga ggctggagtt ggtcgcagcc attaatagta atggtggtag cacctactat   180
ccagacactg tgaagggccg attcaccatc tccagagaca tgccaagaa caccctgtac    240
ctgcaaatga gcagtctgaa gtctgaggac acagccttgt attactgtgc aagacagggg   300
tatggtaact tctttgacta ctggggccaa ggcaccactc tcacagtctc ctca         354
```

<210> SEQ ID NO 20
<211> LENGTH: 339
<212> TYPE: DNA
<213> ORGANISM: Artificial Sequence
<220> FEATURE:
<223> OTHER INFORMATION: Light Chain Variable Region

<400> SEQUENCE: 20

```
gatgttgtga tgacccaaac tccactctcc ctgcctgtca gtcttggaga tcaagcctcc    60
atctcttgta gatctagtca gagcattgta cacagtaatg gaaacaccta tttatattgg   120
tacctgcaga aaccaggcca gtctccaaag ctcctgatct acagggtttc caaccgattt   180
tctggggtcc cagacaggtt cagtggcagt ggatcaggga cagatttcac actcaagatc   240
agcagagtgg aggctgagga tatgggagtt tattactgct ttcaaggtac acatgttcct   300
cggacgttcg gtggaggcac caacttggaa atcaaacgg                          339
```

<210> SEQ ID NO 21
<211> LENGTH: 144
<212> TYPE: PRT
<213> ORGANISM: Homo sapiens

<400> SEQUENCE: 21

```
Met Lys Thr Leu Leu Leu Ala Val Ile Met Ile Phe Gly Leu Leu
1               5                   10                  15

Gln Ala His Gly Asn Leu Val Asn Phe His Arg Met Ile Lys Leu Thr
                20                  25                  30

Thr Gly Lys Glu Ala Ala Leu Ser Tyr Gly Phe Tyr Gly Cys His Cys
            35                  40                  45

Gly Val Gly Gly Arg Gly Ser Pro Lys Asp Ala Thr Asp Arg Cys Cys
        50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95

Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
        115                 120                 125
```

```
Tyr Gln Tyr Tyr Ser Asn Lys His Cys Arg Gly Ser Thr Pro Arg Cys
    130                 135                 140

<210> SEQ ID NO 22
<211> LENGTH: 144
<212> TYPE: PRT
<213> ORGANISM: Homo sapiens

<400> SEQUENCE: 22

Met Lys Thr Leu Leu Leu Leu Ala Val Ile Met Ile Phe Gly Leu Leu
1               5                   10                  15

Gln Ala His Gly Ala Leu Val Asn Phe His Arg Met Ile Lys Leu Thr
                20                  25                  30

Thr Gly Lys Glu Ala Ala Leu Ser Tyr Gly Phe Tyr Gly Cys His Cys
            35                  40                  45

Gly Val Gly Gly Arg Gly Ser Pro Lys Asp Ala Thr Asp Arg Cys Cys
        50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95

Cys Ala Lys Gln Asp Ser Cys Arg Ser Gln Leu Cys Glu Cys Asp Lys
                100                 105                 110

Ala Ala Ala Thr Cys Phe Ala Arg Asn Lys Thr Thr Tyr Asn Lys Lys
            115                 120                 125

Tyr Gln Tyr Tyr Ser Asn Lys His Cys Arg Gly Ser Thr Pro Arg Cys
    130                 135                 140
```